United States Patent [19]
Manimaran et al.

[11] Patent Number: 6,147,264
[45] Date of Patent: Nov. 14, 2000

[54] PROCESS FOR PRODUCING TETRABROMOBISPHENOL-A

[75] Inventors: Thanikavelu Manimaran; Richard A. Holub; Randall S. Barton, all of Baton Rouge, La.

[73] Assignee: Albemarle Corporation, Richmond, Va.

[21] Appl. No.: 09/288,195

[22] Filed: Apr. 8, 1999

[51] Int. Cl.[7] .................................................. C07C 39/16
[52] U.S. Cl. ......................................................... 568/726
[58] Field of Search ............................................. 568/726

[56] References Cited

U.S. PATENT DOCUMENTS

| | | | |
|---|---|---|---|
| 2,455,652 | 12/1948 | Bralley et al. | 260/77.5 |
| 3,029,291 | 4/1962 | Dietzler | 260/619 |
| 3,143,575 | 8/1964 | Bryner et al. | 260/619 |
| 3,182,088 | 5/1965 | Hennis | 260/619 |
| 3,234,289 | 2/1966 | Hennis | 260/619 |
| 3,363,007 | 1/1968 | Majewski et al. | 260/619 |
| 3,546,302 | 12/1970 | Asadorian et al. | 260/619 |
| 3,868,423 | 2/1975 | Montanari et al. | 260/619 A |
| 3,929,907 | 12/1975 | Janzon et al. | 260/619 R |
| 4,013,728 | 3/1977 | Brackenridge | 260/619 A |
| 4,036,894 | 7/1977 | Jenkner | 260/619 A |
| 4,112,242 | 9/1978 | Swietoslawski et al. | 568/726 |
| 4,180,684 | 12/1979 | Kleinschmit et al. | 568/726 |
| 4,282,391 | 8/1981 | Quinn et al. | 568/726 |
| 4,283,566 | 8/1981 | Mark | 568/726 |
| 4,291,177 | 9/1981 | Mark et al. | 568/726 |
| 4,302,614 | 11/1981 | Dannenberg et al. | 568/641 |
| 4,451,675 | 5/1984 | Bounds | 568/726 |
| 4,628,124 | 12/1986 | McKinnie et al. | 568/726 |
| 4,692,555 | 9/1987 | Shin | 568/722 |
| 4,701,568 | 10/1987 | McKinnie et al. | 568/726 |
| 4,783,556 | 11/1988 | Mitchell et al. | 568/726 |
| 4,909,409 | 3/1990 | Mitchell et al. | 422/225 |
| 4,990,321 | 2/1991 | Sato et al. | 423/486 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/226 |
| 5,059,726 | 10/1991 | Eguchi et al. | 568/726 |
| 5,068,463 | 11/1991 | Walter | 568/726 |
| 5,107,035 | 4/1992 | Hines et al. | 568/726 |
| 5,138,103 | 8/1992 | Eguchi et al. | 568/726 |
| 5,208,389 | 5/1993 | McKinnie et al. | 568/726 |
| 5,237,112 | 8/1993 | LaRose | 568/726 |
| 5,283,375 | 2/1994 | McKinnie et al. | 568/726 |
| 5,302,761 | 4/1994 | Tambayashi et al. | 568/726 |
| 5,446,212 | 8/1995 | Sanders | 568/726 |
| 5,527,971 | 6/1996 | McKinnie | 568/726 |
| 5,723,690 | 3/1998 | McKinnie | 568/726 |
| 5,847,232 | 12/1998 | McKinnie | 568/726 |
| 6,002,050 | 12/1999 | McKinnie | 568/726 |

FOREIGN PATENT DOCUMENTS

| | | |
|---|---|---|
| 686772 | 5/1964 | Canada . |
| 706433 | 3/1965 | Canada . |
| 0367869 | 5/1990 | European Pat. Off. . |
| 0380363 | 8/1990 | European Pat. Off. . |
| 0380365 | 8/1990 | European Pat. Off. . |
| 0472395 | 2/1992 | European Pat. Off. . |
| 0572154 | 12/1993 | European Pat. Off. . |
| 0574031 | 12/1993 | European Pat. Off. . |
| 2274586 | 1/1976 | France . |
| 64410 | 11/1981 | Israel . |
| 58-225034 | 12/1983 | Japan . |
| 60-58728 | 12/1985 | Japan . |
| 62-48641 | 3/1987 | Japan . |
| 63-316748 | 12/1988 | Japan . |
| 2196747 | 8/1990 | Japan . |
| 4099743 | 3/1992 | Japan . |
| 5213804 | 8/1993 | Japan . |
| 5229976 | 9/1993 | Japan . |
| 2026280 | 1/1995 | Russian Federation . |
| 949306 | 2/1964 | United Kingdom . |
| 1031500 | 6/1966 | United Kingdom . |
| 1316415 | 5/1973 | United Kingdom . |
| 9620911 | 7/1996 | WIPO . |

OTHER PUBLICATIONS

Chemical Abstracts vol. 78, 1973, p. 328.

Chemical Abstracts vol. 96, 1982, p. 718.

Chemical Abstracts vol. 104, 1986, p. 656.

Chemical Abstracts vol. 104, 1986, p. 716.

Islam et al., "Tetrahalogenated 4:4'—Dihydroxydiphenylalkanes, their Synthesis and some of their Reactions", Egypt J. Chem., vol. 20, No. 5, 1977, ppg. 483–490.

Sadygov et al., "Oxidative Bromination of 2,2–Bis(4'—Hydroxyphenyl) Propane", Neftekhimiya, vol. 30, No. 1, 1990, pp. 109–113. (Translation attached p. 1–7).

Levenspiel Chemical Reaction Eng. (1962), Chapter 6, p. 126, 1962.

Patent Abstracts of Japan, Publication No. JP 62048641, Publication Date Mar. 3, 1987, entitled "Bromination of Bisphenol Compound".

Chemical Abstract, vol. 86, 1977, pp. 570, JP 77,05745.

CAPLUS, Abstract of JP 52,034620, 1977.

WPIDS, Abstract of JP 77/034620, 1977.

JAPIO, Abstract of JP 52,005745, 1977.

*Primary Examiner*—Michael L. Shippen
*Attorney, Agent, or Firm*—E. E. Spielman, Jr.

[57] ABSTRACT

Bisphenol-A or preferably, a mixture of bisphenol-A and underbrominated bisphenol-A, is brominated in a liquid phase reaction medium in which tetrabromobisphenol-A is relatively insoluble, using a stoichiometric deficiency of bromine to thereby form in the reaction mass a precipitate (i.e., a solids phase) composed of 50–95 wt % of tetrabromobisphenol-A and 50-5 wt % of underbrominated bisphenol-A. The precipitate is separated from the reaction mass, preferably during the bromination, and tetrabromobisphenol-A is recovered from the precipitate. Preferably underbrominated bisphenol-A is recycled as feed to the bromination. The process technology of this invention has the capability of producing high quality tetrabromobisphenol-A (high purity, good color, low ionic halide content) with efficient raw material utilization, minimized waste product formation, and minimized waste disposal costs.

43 Claims, 1 Drawing Sheet

PROCESS FOR PRODUCING TETRABROMOBISPHENOL-A

BACKGROUND

Tetrabromobisphenol-A is one of the most widely used brominated flame retardants in the world. It is used extensively to provide flame retardation for styrenic thermoplastics and for some thermoset resins.

Processes used for producing tetrabromobisphenol-A generally fall into three categories. The first category includes processes in which substantial amounts of methyl bromide are co-produced along with the tetrabromobisphenol-A. Generally, up to 40–50 pounds of methyl bromide can be expected per 100 pounds of tetrabromobisphenol-A produced. In most cases, the processes within this first category feature reacting bisphenol-A and bromine in methanol. The ar-bromination of the bisphenol-A is a substitution reaction which generates one mole of HBr per ar-bromination site. Thus, for the production of tetrabromobisphenol-A, four moles of HBr are generated per mole of tetrabromobisphenol-A produced. The HBr in turn reacts with the methanol solvent to produce the methyl bromide co-product. After the bisphenol-A and bromine feed are finished, the reactor contents are cooked for one to two hours to complete the reaction. At the end of the reaction, water is added to the reactor contents to precipitate out the desired tetrabromobisphenol-A product.

The second category of processes features the production of tetrabromobisphenol-A without the co-production of substantial amounts of methyl bromide and without the use of oxidants to convert the HBr to $Br_2$. See for example U.S. Pat. No. 4,990,321; U.S. Pat. No. 5,008,469; U.S. Pat. No. 5,059,726; and U.S. Pat. No. 5,138,103. Generally, these processes brominate the bisphenol-A at a low temperature, e.g., 0 to 20° C., in the presence of a methanol solvent and a specified amount of water. The water and low temperature attenuate the production of methyl bromide by slowing the reaction between methanol and HBr. The amount of water used, however, is not so large as to cause the precipitation of the tetrabromobisphenol-A from the reaction mass. Additional water for that purpose is added at the end of the reaction. This type of process typically uses a fairly long aging or cook period after the reactants have all been fed, and requires additional process time for the final precipitation of tetrabromobisphenol-A via the last water addition.

In the third category are those processes which feature the bromination of bisphenol-A with bromine in the presence of a solvent and, optionally, an oxidant, e.g., $H_2O_2$, $Cl_2$, etc. See for example U.S. Pat. No. 3,929,907; U.S. Pat. No. 4,180,684; U.S. Pat. No. 5,068,463 and Japanese 77/034620 B4 77/09/05. The solvent is generally a water-immiscible halogenated organic compound. Water is used in the reaction mass to provide a two-phase system. As the bisphenol-A is brominated, the tetrabromobisphenol-A is found in the solvent. The co-produced HBr is present in the water. When used, the oxidant oxidizes the HBr to $Br_2$, which in turn is then available to brominate more bisphenol-A and its underbrominated species. By oxidizing the HBr to $Br_2$, only about two moles of $Br_2$ feed are needed per mole of bisphenol-A fed to the reactor. To recover the tetrabromobisphenol-A from the solvent, the solution is cooled until tetrabromobisphenol-A precipitation occurs. The cooling of the solution to recover tetrabromobisphenol-A entails additional expense and process time.

Other problems can be encountered in the development of new technology for tetrabromobisphenol-A production. During bromination, problems may arise because of excessive cleavage of bisphenol-A and/or the several brominated analogs of bisphenol-A. Besides loss of bisphenol-A raw material, such cleavage typically results in loss of bromine due to consequent coproduction of brominated phenols such as tribromophenol. Discoloration of tetrabromobisphenol-A due to presence of colored species in the product is another potential problem that can be encountered. And as is often the case in commercial processing, the formation of significant amounts of undesirable waste products and consequent expense of suitable waste product disposal is still another area of concern.

BRIEF SUMMARY OF THE INVENTION

This invention provides new process technology capable of producing tetrabromobisphenol-A while minimizing some if not all of the foregoing problems. This invention makes it possible to suppress cleavage of bisphenol-A and/or brominated bisphenol-A compounds during production, and to minimize co-production of bromophenols such as tribromophenol. In addition, this invention makes it possible to produce high purity tetrabromobisphenol-A having little or no discoloration. Also, the process produces co-products which are readily recovered and which can be directly used (e.g., by recycle) as intermediates for producing tetrabromobisphenol-A. Thus, the process technology of this invention has the capability of producing high quality tetrabromobisphenol-A (high purity, good color, low ionics content) with efficient raw material utilization, minimized waste product formation, and minimized waste disposal costs.

In one of its embodiments this invention provides a process for the preparation of tetrabromobisphenol-A, which process comprises:

a) brominating bisphenol-A or preferably, a mixture of bisphenol-A and underbrominated bisphenol-A, in a liquid phase reaction medium in which tetrabromobisphenol-A is relatively insoluble, using a stoichiometric deficiency of bromine to thereby form in the reaction mass a precipitate (i.e., a solids phase) consisting essentially of about 50 to about 95 wt % of tetrabromobisphenol-A and about 50 to about 5 wt % of underbrominated bisphenol-A, and preferably about 80 to about 95 wt % of tetrabromobisphenol-A and about 20 to about 5 wt % of underbrominated bisphenol-A;

b) recovering precipitate from the reaction mass; and c) recovering tetrabromobisphenol-A from the precipitate.

The rate and efficiency of precipitate formation in a) are enhanced by including water in the medium used in a). Preferably the liquid phase reaction medium in a) is comprised predominately of water and a water-miscible solvent, especially an alcohol such as methanol or ethanol. When a water-miscible alcohol is used as the water-miscible solvent, the co-presence of the water in the medium of a) is believed to suppress formation of alkyl bromide and waste of bromine that would otherwise result from a side-reaction between the alcohol and HBr co-product from the bromination. Most preferred as the medium in a) is a mixture of ethanol and water wherein the water:ethanol weight ratio in the reaction mass is maintained substantially within the range of about 15:85 to about 70:30 during the bromination in a).

Overall efficiency of the above process operations can be increased by recovering the precipitate from the reaction mass at least periodically during the bromination being conducted in a), and more preferably by separating the precipitate continuously or substantially continuously as precipitate is being formed during the bromination being conducted in a). Preferably, a portion of the reaction mass is removed from the bromination zone or reactor along with the precipitate being removed, as this enables the concurrent introduction or feed of additional reactants into the bromination zone or reactor. Most preferably, the total volume of the feeds to the reactor and the volume of the precipitate and portion of the reaction mass removed from the reactor are controlled to keep the volume of the reaction mass in the reactor substantially constant throughout substantially the entire bromination reaction.

Other embodiments and features of this invention will be still further apparent from the ensuing description, the appended claims and the accompanying drawing.

FURTHER DETAILED DESCRIPTION OF THE INVENTION

Figure 1:
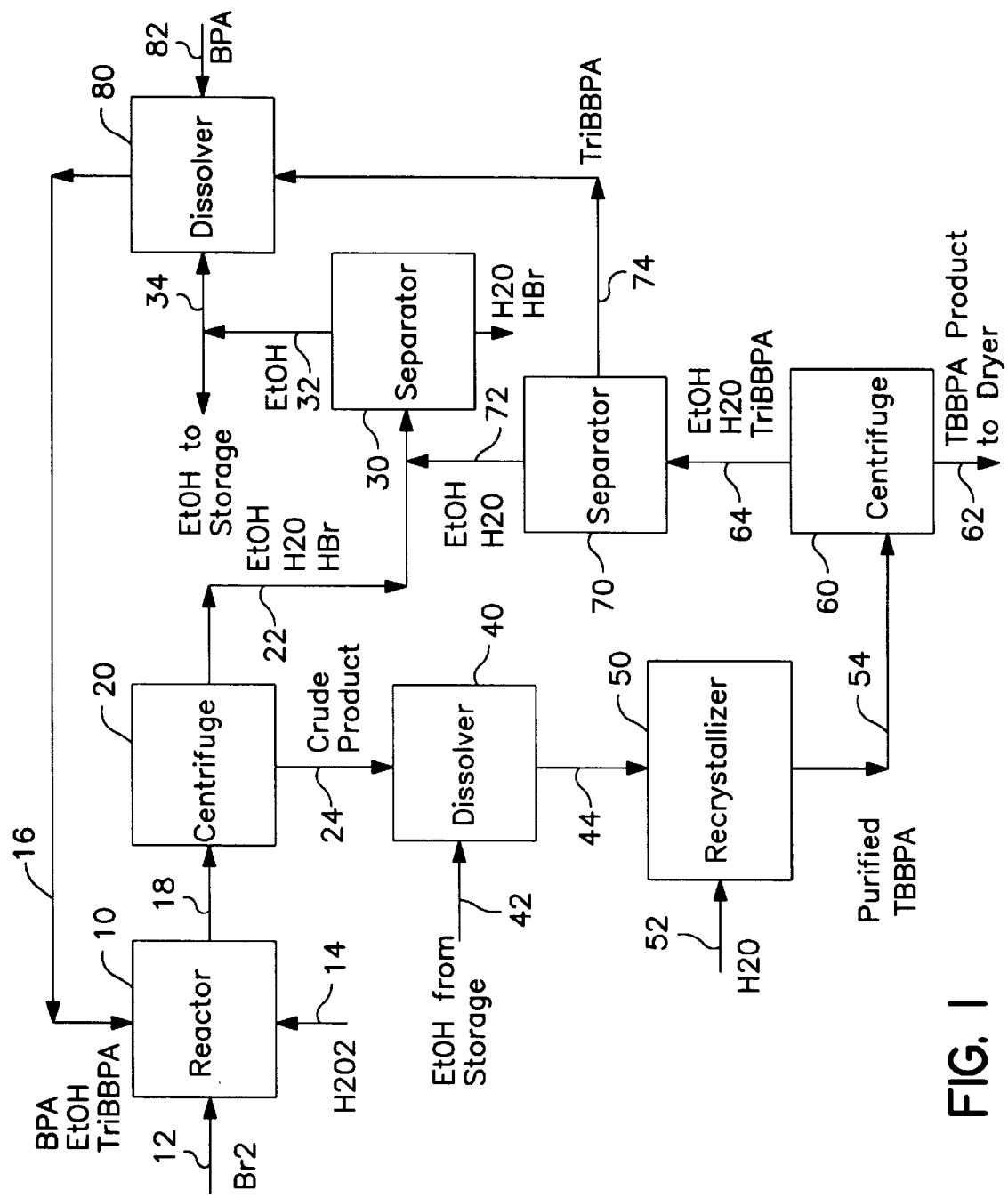
FIG. 1 is a process flow diagram schematically depicting one preferred way of carrying a process embodiment of this invention wherein recycle of underbrominated bisphenol-A, and in situ oxidation of hydrogen bromide co-product to form bromine in situ are both utilized in the operation.

One of the unique features of this invention is the deliberate formation in the bromination reaction of a combination of tetrabromobisphenol-A and underbrominated bisphenol-A. This makes it possible to prepare tetrabromobisphenol-A with virtually no adverse color characteristics, while at the same time suppressing product cleavage and formation of undesirable impurities such as brominated phenols. In this connection, the term "underbrominated bisphenol-A" refers to one or more brominated bisphenol-A compounds in which less than the 4 ortho-positions relative to the hydroxyl groups are substituted by a bromine atom. Typically, the major underbrominated bisphenol-A species is the tribrominated species (3,5-dibromo-4-hydroxyphenyl)(3-bromo-4-hydroxyphenyl)dimethylmethane), but one or more other underbrominated species may be present such as either or both of the dibromo species, 3,5-dibromo-4-hydroxyphenyl)(4-hydroxyphenyl)di-methylmethane and bis(3-bromo-4-hydroxyphenyl)dimethylmethane, and/or the monobromo species (3-bromo-4-hydroxyphenyl)(4-hydroxyphenyl)dimethylmethane.

Process operations of this invention can be run in the batch mode or in the continuous mode. When run in the batch mode, process efficiency is enhanced due to relatively short reactor times as there is no need for a time-consuming one hour plus post-reaction cook period or a post-reaction tetrabromobisphenol-A precipitation step. The use of a continuous process for the production of tetrabromobisphenol-A is indeed a rarity, and is made possible by the short reaction and tetrabromobisphenol-A precipitation times, and use of recycle of underbrominated bisphenol-A intermediates which serve as precursors for the tetrabromobisphenol-A, all of which are features of continuous processes of this invention. In the continuous mode, reactor size can be substantially reduced without a loss in product output.

In addition to the above reaction efficiencies, the processes of this invention are capable of producing good overall yields of tetrabromobisphenol-A even though a stoichiometric deficiency of bromine is present at any given time in the reaction mass. For example, if bisphenol-A, but no underbrominated bisphenol-A, is used as the feed to the bromination reactor, less than 4 moles of $Br_2$ per mole of bisphenol-A is fed to the reactor. If in such case all of the hydrogen bromide co-produced in the bromination reaction is converted in situ to bromine ($Br_2$), the amount of bromine fed to the reactor will be less than 2 moles (e.g., about 1.50 to about 1.95 moles) per mole of bisphenol-A fed. If on the other hand, no hydrogen bromide is converted in situ to bromine, then the amount of bromine fed to the reactor will typically be in the range of about 3.50 to about 3.95 moles of bromine per mole of bisphenol-A fed. If only a portion of the hydrogen bromide is converted in situ to bromine, the amount of bromine fed will be that which typically provides a total amount of bromine in the range of about 3.50 to about 3.95 moles per mole of bisphenol-A fed to the reactor. To convert the hydrogen bromide to bromine in situ, a suitable oxidizing agent is introduced into the reaction mixture.

In the preferred case where both bisphenol-A and underbrominated bisphenol-A are fed to the bromination reactor, again a stoichiometric deficiency of bromine is present at any given time in the reactor. A stoichiometric amount of bromine would be one molecule of diatomic bromine ($Br_2$) for each hydrogen atom present as a substituent in an ortho-position relative to the hydroxyl groups of bisphenol-A and underbrominated bisphenol-A fed to the reactor. For example, if the feed were 1 mole of bisphenol-A and 1 mole of tribromobisphenol-A, there would be a total of 5 moles of such ortho-substituted hydrogen atoms—i.e., 4 moles in the bisphenol-A and 1 mole in the tribromobisphenol-A. A stoichiometric amount of bromine in this particular case would therefore be equivalent to 5 moles of diatomic bromine, and pursuant to this invention an amount of bromine equivalent to less than 5 moles of bromine would be fed, or fed and generated in situ. When the feed includes both bisphenol-A and underbrominated bisphenol-A, the amount of bromine fed (without generation of bromine in situ) or the total amount of bromine fed and generated in situ typically will be in the range of about 80 to about 99% of the stoichiometric amount, and preferably in the range of about 87.5 to about 98.8% of the stoichiometric amount.

Accordingly, another embodiment of this invention is a process which comprises:

a) feeding to a reactor at least bisphenol-A, underbrominated bisphenol-A, a water-miscible solvent, bromine, and water to at least partially form a reaction mass having a liquid phase in which tetrabromobisphenol-A is relatively insoluble;

b) substantially throughout the feed in a), providing for the presence of a stoichiometric deficiency of bromine relative to the bisphenol-A and underbrominated bisphenol-A to thereby form in the reaction mass, a precipitate consisting essentially of about 50 to about 95 wt % of tetrabromobisphenol-A and about 50 to about 5 wt % of underbrominated bisphenol-A, and preferably a precipitate consisting essentially of about 80 to about 95 wt % of tetrabromobisphenol-A, about 20 to about 5 wt % of underbrominated bisphenol-A, and, if any, no more than about 0.1 wt % of tribromophenol;

c) removing precipitate and optionally but preferably a portion of the reaction mass from the reactor; and d) separating tetrabromobisphenol-A and underbrominated bisphenol-A from each other.

The separated underbrominated bisphenol-A is preferably recycled as feed in a).

There are various ways of separating tetrabromobisphenol-A and underbrominated bisphenol-A from each other. One preferred way involves recrystallizing tetrabromobisphenol-A from a solution of tetrabromobisphenol-A and underbrominated bisphenol-A, and separating the recrystallized tetrabromobisphenol-A from the residual solution of underbrominated bisphenol-A. For example, the reaction mass including precipitate removed from the reactor can be decanted, filtered, centrifuged, or otherwise processed to separate the solids from the liquid phase. The solids can then be dissolved in a suitable water-miscible solvent such as a lower alcohol (e.g., ethanol), heated and treated while hot with water. On cooling, purified tetrabromobisphenol-A recrystallizes from the solution. The recrystallized tetrabromobisphenol-A has a very low content, if any, of ionic bromide impurities. The resultant slurry is then decanted, filtered, centrifuged, or otherwise processed to separate the purified tetrabromobisphenol-A solids from the liquid phase which contains the underbrominated bisphenol-A which remains in solution. After separating all or at least a portion of the water-miscible solvent and water from the underbrominated bisphenol-A, the water-miscible solvent can be separated from the water, such as by distillation and is available for reuse. Preferably, the water-miscible solvent used in the bromination reaction and the water-miscible alcohol used in forming the solution from which tetrabromobisphenol-A is recrystallized are the same kind of solvents, i.e., whatever one is, the other is. Most preferably, these two solvents are water-miscible alcohols of the formula ROH where the R is an alkyl group and where the alkyl group in both such solvents is the same. Ethanol is most preferred. The underbrominated bisphenol-A is recycled as feed to the bromination reaction, and the recovered water-miscible solvent is available for reuse, preferably as solvent in the bromination reaction. Examples II and III hereinafter illustrate the separation and recovery of tetrabromobisphenol-A and a solution of underbrominated bisphenol-A by recrystallization using ethanol as the solvent.

Other ways of separating tetrabromobisphenol-A and underbrominated bisphenol-A include adsorption methods (e.g., chromatography) and preferential extraction or leaching methods using suitable solvents.

The benefits realized by converting the hydrogen bromide in situ to bromine can be obtained pursuant to a preferred embodiment of this invention by (1) brominating bisphenol-A with a stoichiometric deficiency of brominating agent in the presence of a water-miscible solvent, e.g., methanol or ethanol, and a relatively large amount of water while maintaining the reaction mass at a suitable reaction temperature and, concurrent therewith, (2) oxidizing HBr produced in the reaction mass to $Br_2$ for use in the bromination. An especially desirable way of conducting such an operation comprises:

a) feeding to a reactor at least bisphenol-A, a water-miscible solvent, bromine, water, and an oxidant to at least partially form a reaction mass having a liquid phase in which tetrabromobisphenol-A is relatively insoluble;

b) substantially throughout the feed in a), providing for the presence of a stoichiometric deficiency of bromine relative to the bisphenol-A and underbrominated bisphenol-A to thereby form in the reaction mass, a precipitate consisting essentially of about 50 to about 95 wt % of tetrabromobisphenol-A and about 50 to about 5 wt % of underbrominated bisphenol-A, and preferably a precipitate consisting essentially of about 80 to about 95 wt % of tetrabromobisphenol-A, about 20 to about 5 wt % of underbrominated bisphenol-A, and, if any, no more than about 0.1 wt % of tribromophenol;

c) removing precipitate and optionally a portion of the reaction mass from the reactor; and d) separating tetrabromobisphenol-A and underbrominated bisphenol-A from each other.

The underbrominated bisphenol-A is thus available for use as feed to the reactor. Therefore, most preferably, the feed in a) further comprises underbrominated bisphenol-A. In such case the stoichiometric deficiency of bromine used pursuant to this invention is based on the bisphenol-A and underbrominated bisphenols being fed in a), as noted above.

Another very desirable way of carrying out the bromination and concurrent in situ generation of bromine by in situ oxidation of hydrogen bromide substantially as soon as it is formed in the reaction mass comprises the following steps:

a) feeding, to a reactor, a solution comprised of bisphenol-A, water and a water-miscible solvent to at least partially form a reaction mass having a liquid phase containing an amount of water in the range of from above about 15 to about 65 wt % water that renders tetrabromobisphenol-A substantially insoluble in said liquid phase, the wt % being based upon the amount of water and water-miscible solvent in the liquid phase;

b) during a), providing for the presence of $Br_2$ in the reaction mass to produce tetrabromobisphenol-A and HBr co-product;

c) oxidizing HBr produced in the reaction mass to yield $Br_2$;

d) having a reaction mass temperature which is within the range of from about 50 to about 100° C.;

e) keeping the total amount of bromine provided in a) and produced in c) sufficiently below the stoichiometric amount required to convert all of the bisphenol-A present in the reactor to tetrabromobisphenol-A so that a precipitate is formed composed of about 50 to about 95 wt % of tetrabromobisphenol-A and about 50 to about 5 wt % of underbrominated bisphenol-A, and preferably about 80 to about 95 wt % of tetrabromobisphenol-A, about 20 to about 5 wt % of underbrominated bisphenol-A, and, if any, no more than about 0.1 wt % of tribromophenol.

The precipitate, preferably along with a portion of the reaction mass, is removed from the reactor, most preferably concurrent with the bromination taking place in the reactor. The tetrabromobisphenol-A is then recovered from the precipitate, and underbrominated bisphenol-A is available for use as feed to the reactor. Thus the feed in a) most preferably is further comprised of underbrominated bisphenol-A. Thus here again, the stoichiometric deficiency of bromine used pursuant to this invention is based on the bisphenol-A and underbrominated bis-phenols being fed in a).

In each of the above embodiments wherein a) specifies "feeding," it is preferred to conduct this operation as a "co-feeding" operation. Such co-feeds to the reactor can be separate feeds of (i) bromine and (ii) a solution comprised of bisphenol-A, water and a water-miscible solvent. Alternatively the feeds can be separate feeds of (i) bromine, (ii) a solution comprised of bisphenol-A, water and a water-miscible solvent, and (iii) a feed comprised of underbrominated bisphenol-A. A variant of this latter feeding arrangement is to include the underbrominated bisphenol-A with the bisphenol-A feed so that the separate co-feeds are (i) bromine and (ii) a mixture comprised of bisphenol-A, underbrominated bisphenol-A, water and a water-miscible solvent. Of course other ways of co-feeding these materials can be envisioned, but those just described are deemed most cost-effective for a commercial facility. As regards the timing aspects of the co-feeding, the foregoing separate feeds will occur during periods that overlap one another to at least some extent. For example, in a batch type operation, the feed of bisphenol-A and underbrominated bisphenol-A can be initiated and then followed by initiation of the other feed or feeds, with both or if three separate feeds are employed, all three feeds thereafter occurring simultaneously until at least one of them is finished. Another example would be that of an initial $Br_2$ feed followed by a continuous solution feed which is accompanied by a continued, but intermittently interrupted or staged, $Br_2$ feed. Yet another example is that of initiating the $Br_2$ feed after initiation of the other feed or feeds so that the two or three feeds occur simultaneously for at least a portion of the time required to feed the reactants. Other co-feed schemes can feature (1) an intermittently interrupted feed of the bisphenol-A solution and/or (2) an intermittently interrupted feed of a separate feed of underbrominated bisphenol-A and/or (3) an intermittently interrupted combined feed of bisphenol-A, underbrominated bisphenol-A, water and a water-miscible solvent. However, no matter whether these or still other co-feeding schemes are used, the relative proportions of the feeds are maintained such that there exists a stoichiometric deficiency of bromine relative to bisphenol-A, and a stoichiometric deficiency of bromine relative to bisphenol-A and underbrominated bisphenol-A when the latter is included as a feed component, so that less than all of the bisphenol-A and/or underbrominated bisphenol-A is converted to tetrabromobisphenol-A. Preferably such stoichiometric deficiency is maintained throughout substantially the entire reaction period.

In continuous modes of operation it is possible to employ staged or interrupted co-feeding techniques. However, it is generally preferred to establish and maintain steady state operation wherein the feed of bisphenol-A and recycled of underbrominated bisphenol-A, whether fed as separate feed streams or as a unified feed stream, are maintained at a stoichiometric excess relative to the bromine so that once steady-state bromination has been established and is proceeding, the bromination reaction mass always contains a mixture of tetrabromobisphenol-A and underbrominated bisphenol-A.

Feeds that do not have some overlap between the duration of the $Br_2$ feed and the duration of the feed or feeds of the other reactants are possible, but will not be generally preferred. For example, all of the bisphenol-A and underbrominated bisphenol-A (if used) can be fed followed by the feed of bromine. However, depending on reaction conditions, such a feed scheme could lead to the formation of an excessive amount of underbrominated bisphenol-A relative to the amount of tetrabromobisphenol-A produced due to precipitation of substantial amounts of tribromobisphenol-A.

Regardless of the feeding protocol used, it must be such that the bromination results in the co-production in the reaction mass of tetrabromobisphenol-A and underbrominated bisphenol-A. Preferably these products are formed in proportions such that at least about 70 mole percent and no more than about 97 mole percent of the total tetrabromobisphenol-A and underbrominated bisphenol A in the reaction mass is tetrabromobisphenol-A. More preferably, of the total tetrabromobisphenol-A and underbrominated bisphenol-A in the reaction mass, at least about 85 mole percent and not more than about 95 mole percent is tetrabromobisphenol-A.

Commercially available bromine is suitable for use as the bromine feed. If the bromine contains undesirable impurities, it can be treated by conventional purification techniques, e.g., distillation, $H_2SO_4$ treatment, etc., which are well known to those skilled in the art.

Bromine can be fed as a liquid or as a gas to the reactor. It is preferred that the feed be gaseous. Whether bromine is liquid or gaseous, it is preferred that the feed entry point be sub-surface of the reaction mass. This is conveniently accomplished by use of a dip tube. If the feed is liquid, above-surface feed must contend with possible splattering and inefficient mixing.

The amount of water in the reaction mass should be within the range of from above about 15 to about 65 wt % water based upon the total amount of water and water-miscible solvent in the liquid phase of the reaction mass. Preferably, the amount of water fed is that amount which is within the range of from about 25 to about 65 wt % water. Most highly preferred is the range of from about 25 to about 50 wt %. When the water-miscible solvent is methanol, the preferred amount of water is from about 30 wt % to about 45 wt %. When the water-miscible solvent is ethanol, the preferred amount of water is from about 40 wt % to about 50 wt %.

The water content of the reaction mass is an important aspect of this invention as it results in a liquid phase in which tetrabromobisphenol-A and at least some of the underbrominated bisphenol-A are relatively insoluble. Also, it is believed that the water content of a mixture of water and a water-miscible alcohol suppresses formation of alkyl bromide. Although the processes of this invention are not to be limited by any particular theory, it is believed that such alkyl bromide formation is suppressed because HBr, which is co-produced by the substitution bromination reaction between bisphenol-A and $Br_2$, is diluted by the large amount of water in the reaction mass. Further, at least some of the HBr is believed to react with the water to yield $H_3OBr$ which is very slow to react with a water-miscible alcohol solvent, e.g., methanol or ethanol.

The water being fed to the reactor has heretofore been described as being part of a solution which also contains bisphenol-A and a water-miscible solvent. Feeding the water as part of such a solution is convenient and preferred. However, the water may be introduced into the reaction mass in other equivalent ways. For example, the water can be fed as a separate feed stream. Such a feed could be essentially contemporaneous with the feed of a solution of bisphenol-A and water-miscible solvent. Even further, a portion, if not all, of the water can be fed as steam or steam condensate along with a gaseous $Br_2$ feed. The steam could have been used to vaporize the $Br_2$ to form the gaseous feed. Another example features providing water as a charge or as part of a charge to the reactor prior to initiating the feeds and adjusting the amount of water later fed to obtain the desired water content in the reaction mass. However the water is provided to the reaction mass, the only requirement for the water feed is that it be such that the proper amount of water be present in the reaction mass during substantially all of the reaction period.

In those cases where the amount of water used is in the lower end of the range, say 15 to 25 wt %, it may be desirable to add some additional water at the end of the bisphenol-A bromination. The possible advantage to such an addition is that the additional water may cause further precipitation of tetrabromobisphenol-A from the reaction mass. The further precipitation goes towards increasing the yield of the process. In these cases, the added water is counted in determining the total wt % of water in the solution formed from water and the water-miscible solvent.

The feed of the water-miscible solvent has been described above in conjunction with the feed of the solution. However, the solvent feed need not always be exclusively as a constituent of the solution provided that the functions of the solvent are not hindered. For example, a portion of the solvent can be fed as part of the solution as is needed to solvate the bisphenol-A in the solution, while the remaining portion, generally a smaller portion, can be fed as a separate stream. From a practical standpoint though, the solvent is best fed as a solution constituent.

As can be appreciated from the foregoing, the manner of carrying out the feeding of water, solvent, bisphenol-A, and when used as feed, underbrominated bisphenol-A, is not critical to the processes of this invention provided that the reaction mass is properly constituted. Thus, to simplify matters for discussion, the feed to the reactor, which comprises bisphenol-A, water and water-miscible solvent, and preferably underbrominated bisphenol-A as well, is to mean that the water can be fed as a constituent of a mixed feed stream, as a separate stream, or as a combination of both, and that the solvent can all be fed as a constituent of a mixed feed stream, or a portion of the solvent can be a constituent of one or more mixed feed streams and a portion of the solvent can be fed as a separate stream. Also to be considered as part of the feed is any water or solvent which is provided to the reaction mass as a pre-feed charge or as a part of such a charge to the reactor.

The water-miscible solvent can be defined functionally as a material which is capable of solvating $Br_2$, bisphenol-A, monobromobisphenol-A, dibromobisphenol-A and tribromobisphenol-A under reaction conditions. The reaction conditions of special import are the reaction mass temperature, the presence of a stoichiometric deficiency of $Br_2$ in the reaction mass and the reaction mass water content. Further, the solvent should be substantially inert with regard to $H_3OBr$ and the ar-bromination of the bisphenol-A to tetrabromobisphenol-A, and should not contribute to the production of troublesome amounts of color bodies, ionic bromides and/or hydrolyzable bromides. Hydrolyzable bromides may include 1-bromo-2-alkoxy-2-(3",5"-dibromo-4'-hydroxyphenyl)propane, 1,1-dibromo-2-alkoxy-2-(3',5'-dibromo-4'-hydroxyphenyl)propane, 1,3-dibromo-2-alkoxy-2-(3',5'-dibromo-4'-hydroxyphenyl)propane, and 1,1,3-tribromo-2-alkoxy-2-(3',5'-dibromo-4'-hydroxyphenyl) propane. The solvent, when taken in combination with the water and reaction conditions of the processes of this invention, can have some small ability to solvate tetrabromobisphenol-A, but for the sake of reaction yield, the solvating power should be low, say no more than about 20 wt % and preferably no more than about 5 wt % solvated tetrabromobisphenol-A in the liquid phase of the reaction mass.

Exemplary of the preferred water-miscible solvents are water-miscible alcohols, carboxylic acids, e.g., acetic acid, and nitriles, e.g., acetonitrile. By water-miscible is meant that at the temperature of the bromination the solvent and water are mutually soluble in each other in the proportions actually present in the reactor. Some ethers may also be suitable solvents provided they are not cleaved by the acidic nature of the reaction mass. The more preferred solvents are the alcohols having up to 4 carbon atoms. Most preferred are ethanol and methanol. Methanol and ethanol are relatively inexpensive and are easily recovered by simple distillation techniques for recycle. Since there is a large water presence in the processes of this invention, it is not necessary to recover the methanol or ethanol with a low water content, thereby reducing the methanol or ethanol recovery cost.

The amount of water-miscible solvent used is best related to the amount of bisphenol-A fed and can be conveniently expressed as the weight ratio of the solvent to bisphenol-A. Preferably, the ratio is within the range of from about 2:1 to about 10:1, and most preferably within the range of from about 3:1 to about 5:1. More or less solvent can be used, provided that the solvent function mentioned above is accomplished.

The bromine and other feed streams are preferably at a temperature which promotes process efficiency in view of the desired reaction mass temperature. A suitable liquid $Br_2$ feed temperature is from about 10° C. to just below the boiling point of $Br_2$. If the $Br_2$ is to be fed as a gas, then the $Br_2$ stream temperature should be that which is conducive to such a feed. For example, such a feed temperature may be within the range of from about 60 to about 100° C. The feed temperature(s) of the other feed components should be that which does not detrimentally cool or heat the reaction mass or which requires pressure operation so that the feed can be made in the liquid state. If the solution feed is to be made with separate water and/or solvent feeds, then the same comments made above with regard to temperature apply to the separate feeds.

The bromine and solution and/or separate water, etc., feeds all contribute to the formation of the reaction mass in the reactor. These feeds will produce (a) a reaction mass liquid phase (liquid portion) and, because of the formation of a precipitate of tetrabromobisphenol-A and at least some of the underbrominated bisphenol-A, (b) ultimately a reaction mass solid phase (solid portion). The bromine, whether fed as a liquid or gas or generated in situ by oxidation of HBr, will be consumed in the bromination reaction. Non-consumed bromine, if any, will be found in the liquid phase.

It is permissible for the bromine content in the reaction mass to exceed the stoichiometric amount for brief periods of time depending on the average level of underbrominated bisphenol-A species that are present in the reaction product as the bromination reaction proceeds and/or upon the average proportion of the underbrominated bisphenol-A species in the precipitate formed during the course of the bromination.

Quantifying the optimum preferred stoichiometrically deficient amount of $Br_2$ to be fed to and formed in situ in the reaction mass liquid phase is best handled by a trial and error technique. A trial process is first defined by choosing a stoichiometrically deficient $Br_2$ level relative to the level of bisphenol-A and underbrominated bisphenol-A to be present in the reaction mass, and the other process parameters to be employed. The produced tetrabromobisphenol-A product from the process is analyzed for its tribromobisphenol-A and tetrabromobisphenol-A contents. If the tribromobisphenol-A level is too low, another trial process is constructed with a lower $Br_2$ level in the reaction mass. The procedure is repeated until the desired product is obtained. It is to be noted that some benefit towards increasing the tribromobisphenol-A content of the precipitate can also be obtained by using a lower reaction temperature. As the chosen $Br_2$ level gets lower, care should be taken that the $Br_2$ level will not be so low that it results in the production of an amount of tetrabromobisphenol A that is too low for the overall process (e.g., including recycle in or to a second bromination) to be economically viable.

A rough assessment of the $Br_2$ content of the reaction mass relative to-the reactants being brominated can be accomplished by visually observing the reaction mixture as the bromination is proceeding. If a reddish, reddish-orange, or even yellowish hue of bromine is present at all times, the level of bromine in the reaction mass is too high. Note, however, that there is no requirement that the reaction mass must be colorless at all times during the bromination, especially in a batch type operation. Moreover, if the reaction mass is colorless at all times, the level of bromine can, of course be too low.

It is also to be understood that the method used to obtain the desired deficient $Br_2$ level in the reaction mass can be by a method other than the adjustment of the before-mentioned feeds. For example, when an oxidant is used to convert HBr to $Br_2$, the amount of $Br_2$ generated in situ can be regulated by controlling the amount of oxidant fed to the reaction mass. The amount of unreacted $Br_2$ contributed to the reaction mass by oxidation of HBr can be substantial considering that three moles of HBr are generated for each mole of tribromobisphenol-A produced, and four moles of HBr are generated for each mole of tetrabromobisphenol-A produced. Thus, for efficient utilization of raw materials, in situ oxidation of HBr to generate at least a part of the $Br_2$ needed to obtain the desired $Br_2$ level.

With the use of an oxidant to oxidize the HBr to $Br_2$, the processes of this invention can obtain good results by feeding a suitable amount less than two moles of $Br_2$ to the reactor for every one mole of bisphenol-A fed. Two moles of the $Br_2$ needed for the bromination can be provided by the full oxidation of the co-generated HBr. If there is less than full HBr oxidation, then the amount of $Br_2$ fed to the reactor will be that amount, in sum with the $Br_2$ formed by oxidation, which will provide stoichiometrically deficient quantities of $Br_2$ and preferably quantities which are in the range of about 80 to about 95 percent of stoichiometric, and more preferably in the range of about 90 to about 95 percent of stoichiometric, stoichiometric $Br_2$ for the ar-tetrabromination of bisphenol-A being four moles of $Br_2$ per mole of bisphenol-A. As can be appreciated, if the oxidation of HBr is not used in the process, then the $Br_2$ feed would be in the range of about 80 to about 95 percent of stoichiometric, and more preferably in the range of about 90 to about 95 percent of stoichiometric.

The oxidant material is any oxidant which is capable of oxidizing HBr to $Br_2$ in the reaction masses and under the process conditions of this invention. Preferred oxidants are those in liquid form which can facilitate their feed to the reactor. Usable oxidants include chlorine, peroxides, hydroperoxides, peroxyesters, peroxycarbonates and similar substances. The preferred oxidants are inorganic peroxides, especially hydrogen peroxide.

When the oxidant is $H_2O_2$, safety makes it preferably that it be fed to the reaction mass in an aqueous solution containing no more than about 90 wt % $H_2O_2$. Preferred are aqueous solutions containing from about 30 to about 80 wt % $H_2O_2$. A most preferred solution is one containing from about 50 to about 70 wt % $H_2O_2$.

The $H_2O_2$ can be fed to the reaction mass at any time. For batch operation, it is preferred that the $H_2O_2$ be fed after most of the $Br_2$, say above about 50%, has been fed. For continuous operation, the $H_2O_2$ feed would most preferably occur contemporaneously with at least most of the $Br_2$ feed. Most preferably, the $H_2O_2$ feed would start after initiating the $Br_2$ feed.

The oxidants can be fed to the reaction mass separately or in some cases, along with the $Br_2$ feed. The preferred oxidant, $H_2O_2$, is preferably fed as a separate feed stream.

The amount of oxidant fed is preferably that amount needed to maximize the amount of HBr oxidized without leaving a large excess of oxidant present in the reaction mass. Assuming that one mole of the oxidant chosen will oxidize two moles of HBr, the mole ratio of oxidant to bisphenol-A fed should be within the range of from about 1:1 to about 2:1. A more preferred mole ratio is from about 1.5:1 to about 1.9:1. The higher oxidant ratios are preferred when $H_2O_2$ is the oxidant, while the mid range ratios, say 1.5–1.8:1 are preferred when $Cl_2$ is the oxidant. The reason that the lower oxidant ratios are preferred for $Cl_2$ is that there is a balance between the amount of HBr oxidized and the amount of chlorobromo species which can be tolerated. If there is no need to keep the chlorobromo species to some minimum amount, then more $Cl_2$ is permissible. Adjustments to the above ranges are necessary if the oxidant chosen does not oxidize the HBr on a one to two basis. In these cases, the ranges are adjusted in proportion to the variance in the one to two relationship.

Another important consideration in practicing the processes of this invention is the reaction mass temperature during the bromination period. It is desirable to use a sufficiently high temperature so that the bromination of the bisphenol-A to tetrabromobisphenol-A and underbrominated bisphenol-A will be sufficiently fast to keep the bromination time or bromination residence time in the reactor from being unduly excessive and economically undesirable. However, there is a practical limit as to how high the temperature can be. For example, the use of temperatures which would cause the production of unacceptable levels of unwanted by-products or the degradation of the desired mixture of tetrabromobisphenol-A and underbrominated bisphenol-A species.

It is unusual in the art to operate a tetrabromobisphenol-A process at relatively high temperatures. This is especially so when the production of a co-product, e.g., methyl bromide or ethyl bromide, is to be minimized, as it is conventional to expect that high temperatures will yield large amounts of methyl bromide. Also, the use of high temperatures is not conventional when the precipitation of the tetrabromobisphenol-A and some underbrominated bisphenol-A is to occur under reaction conditions soon after they are formed, such precipitation being a feature of the processes of this invention. It could be expected that use of relatively high temperatures might frustrate such precipitation by increasing the solubility of the tetrabromobisphenol-A and underbrominated bisphenol-A species in the solvent solution and require a final cooling of or addition of more water to the reaction mass to effect the desired precipitation. The processes of this invention when conducted under preferred conditions are not so affected, nor is there required a cooling step to obtain the desired precipitation of tetrabromobisphenol-A and underbrominated bisphenol-A species.

Thus the preferred temperatures used in the bromination contribute to process economy. Process economy, in part, is realized because, with the preferred reaction mass temperatures used, the process of this invention can use cooling tower water to cool the reactor instead of having to use refrigeration which is required by the low temperature processes.

Preferred temperatures are within the range of from about 30 to about 100° C. The more highly preferred temperatures are within the range of from about 50 to about 65° C., especially when conducting the process as a batch process. Temperatures below 30° C. can be used, but the solvent to bisphenol-A weight ratio may well need to be high, say from 8:1 to 15:1. For these ratios, temperatures of 30 to 50° C. may be suitable.

The bromination of bisphenol-A is an exothermic reaction as is the oxidation of HBr with $H_2O_2$. To control the reaction mass temperature, it may become necessary to remove heat from the reaction mass. Heat removal can be effected by running the reaction at reflux with the condenser facilitating the heat removal. If it is desired to operate at a temperature below the atmospheric boiling point of the reaction mixture, the reaction can be run under sub-atmospheric pressure.

Generally, the basic concepts of the processes of this invention are not appreciably affected by the process pressure. Thus, the process can be run under sub-atmospheric, atmospheric or superatmospheric pressure.

At process initiation, it is desirable to charge the reactor with a liquid pre-reaction charge which will become a part of the reaction mass upon the commencement of the feed. The liquid charge will provide a stirrable reaction mass and act as a heat sink to moderate temperature changes in the reaction mass. The liquid charge is preferably comprised of water and the same water-miscible solvent fed in the solution. It is preferred that the liquid charge be acidic, e.g., containing from 1 to 20 wt % acid such as HBr, HCl or the like. The acid seems to promote good color in the initial tetrabromobisphenol-A produced. Further, it is preferred that the solvent be saturated with solvated tetrabromobisphenol-A. It is also preferred that the reactor be charged with seed particles of tetrabromobisphenol-A. The saturation of the solvent and the presence of the seed particles both act to enhance the precipitation of the tetrabromobisphenol-A and perhaps the co-precipitation of some of the underbrominated bisphenol-A species produced during the bromination period. It is most practical in batch operations to use a heel from a previously run process of this invention as the liquid charge. The tetrabromobisphenol-A seed particles can be brought over from the previous run or can be added separately. If a heel is not available, it is also possible to use a separate water and water-miscible solvent feed, which are a part of the total solution feed, to form the liquid charge. In this scheme, an initial amount of water and water-miscible solvent are fed to the reactor prior to the initiation of the solvated bisphenol-A portion of the solution feed. The only caveat to this scheme is that there must be apportionment of the various feeds making up the solution feed so that there will still be compliance with the various parameters which define the processes of this invention.

If the process of this invention is run as a batch process, the $Br_2$ and other component feeds are fed to a stirred reactor until they are exhausted. There is no need for a post-feed cook period of any significant length as, under the reaction conditions, the bromination of bisphenol-A to a desirable mixture of tetrabromobisphenol-A and underbrominated bisphenol-A occurs quite rapidly. Also, since the water content of the reaction mass is so large and since the tetrabromobisphenol-A and at least some of the underbrominated bisphenol-A is so insoluble in the presence of such an amount of water, there is only a modicum of benefit in cooling the final reaction mass. The benefit of cooling resides mainly in reducing the vapor pressure of solvated gaseous bromides, e.g., methyl bromide or ethyl bromide, if present in the reaction mass prior to the liquid-solids separation. There also could be some slowing of the formation of these bromides. In addition, depending upon the water content of the reaction mass, cooling may allow for additional precipitation of tetrabromobisphenol-A and/or one or more underbrominated bisphenol-A species from the reaction mass. When operating within the preferred ranges recited herein, the additional precipitation benefit may not offset by the expense associated with obtaining the same. Finally, depending on the separation technique used, cooling the reaction mass may make it easier to handle downstream materials from the reactor. Thus, if none of the above are of concern or relative value under the particular circumstances involved, then the reaction mass can be subjected to liquid-solids separation as soon as it can be transported to the separation equipment. If, however, cooling is desired, the cooling time will depend upon how the reaction mass is to be cooled and to what temperature it is to be cooled. In a laboratory setting, cooling times can range from about one to about thirty minutes.

Additional time may also be used between the end of the co-feed and the precipitate recovery, if it is desired, to add additional water to the reaction mass at the end of the co-feed to insure that even more precipitate composed of tetrabromobisphenol-A and/or underbrominated bisphenol-A species is formed in the reaction mass. The water addition and precipitation time can be very short, typically less than about thirty minutes.

Irrespective of whether or not the reaction mass is cooled or treated with more water, it is to be understood that the additional time used does not appreciably increase the total amount of tetrabromobisphenol-A produced by the process (the total amount includes that which is a precipitate and that which is solvated in the reaction mass). These additional times, therefore, are not to be considered cook times in the same way as are the cook times taught by the prior art processes.

Solids recovery can be effected by use of filtration, centrifugation, decantation, or like liquid-solids physical separation procedures.

As noted above, a preferred procedure for separating tetrabromobisphenol-A from underbrominated bisphenol-A in the precipitate involves dissolving the precipitate in a suitable water-miscible organic solvent and crystallizing tetrabromobisphenol-A from the resulting solution. The water-miscible solvent used in this procedure is most preferably the same kind of water-miscible solvent as is used in forming the bromination reaction medium. For example, if ethanol is used as the organic solvent in the bromination reaction medium, then the crystallization solvent is most preferably ethanol. This crystallization procedure can be accomplished by dissolving the precipitate in an amount of the crystallization solvent not substantially in excess of the minimum amount required to dissolve the entire precipitate in the solvent at the temperature of the solvent. Preferably the solvent is at an elevated temperature when dissolving the precipitate therein, and the precipitate and solvent should be well agitated to facilitate solution formation. Then the temperature of the solution is reduced to a temperature at which a solids phase of substantially pure tetrabromobisphenol-A is formed. This precipitate is then recovered by any of suitable liquid-solids separation procedure such as decantation, filtration, centrifugation, or the like. In a preferred variant of this procedure, water is added to the concentrated solution of the precipitate in the crystallization organic solvent, to reduce the solubility of the tetrabromobisphenol-A. The water can be added before, during and/or after cooling the solution, but preferably is added while the organic solution is at an elevated temperature.

The mother liquor resulting from the crystallization procedure contains dissolved underbrominated bisphenol-A. Such solution, after removal of the tetrabromobisphenol-A solids therefrom, is preferably used as recycle to the bromination reaction.

After the recovery of the solids from the liquid, the solids are preferably washed with a solution of water and the particular water-miscible solvent used in the reaction. The washing removes essentially all the mother liquor from the solids. The mother liquor typically contains some tetrabromobisphenol-A and/or a portion of the underbrominated bisphenol-A formed during the reaction together with impurities such as tribromophenol, HBr, and hydrolyzable impurities. A typical wash can be a 30 wt % ethanol in water solution. The washed solids are then rewashed with deionized water to remove any remaining water-miscible solvent from the first wash so as to minimize emission problems when drying the product.

When run in the continuous mode, the reactor is preferably a continuously stirred tank reactor. The reaction mass is being continuously formed and a portion thereof is being removed from the reactor during the reaction mass formation. The reactor design should be such that the average residence time in the reactor is sufficient to insure the tetrabromination of a substantial portion, but not all, of the bisphenol-A. Preferably, the reaction mass exiting from the reactor should contain a precipitate containing in the range of about 80 to about 95 wt % of tetrabromobisphenol-A and about 20 to about 5 wt % of underbrominated bisphenol-A species, both exclusive of any impurities that may also be present therein. The terms "continuous feed" and "continuous withdrawal" are not meant to exclude interrupted feeds or withdrawals. Generally, such interruptions are of short duration and may be suitable depending upon the scale and design of the reactor. For example, since the tetrabromobisphenol-A precipitate will tend to settle near the bottom of the reactor, a withdrawal may be made and then stopped for a period of time to allow for precipitate build-up to occur prior to the next withdrawal. Such a withdrawal is to be considered continuous in the sense that the withdrawal does not await the completion of the reactor feeds as is characteristic of batch processes.

Whether the continuous withdrawal is interrupted or not, the withdrawal results in a portion of the liquid and a portion of the solids in the reaction mass to be withdrawn together. The mixture can be filtered or centrifuged, the solids washed, etc., as is done for the above-described batch mode case.

When using the continuous mode of operation, it is believed that it would be beneficial if the reaction mass temperature were kept fairly high as compared to the temperatures preferred for the batch mode. Preferred batch mode temperatures are from about 50 to about 65° C. For the continuous mode, the preferred temperatures are within the range of from about 50 to about 95° C., and most preferably within the range of from about 55 to about 70° C.

In the continuous mode of operation, the preferred reactor residence time should be within the range of from about 30 to about 150 minutes when using a stirred-tank reactor and the process conditions which are preferred for that operating mode. Reactor residence time, as used here, is the reactor volume divided by the flow rate at which slurry is removed from the reactor.

The tetrabromobisphenol-A product produced by the processes of this invention can have a very high purity—e.g., at least 97 wt % tetrabromobisphenol-A. The tribromobisphenol-A content is low—e.g., from about 0.1 to about 3 wt %. The product quality is excellent, having an APHA color less than about 50 (80 grams of tetrabromobisphenol-A in 100 ml of acetone). Hydrolyzable bromides are also kept low, generally below about 60 ppm. The process yields are impressive, with yields within the range of from about 95 to about 99% being possible.

As can be appreciated from the foregoing, the water content of the solvent, the reaction temperature and the $Br_2$ content in the reaction mass during the bisphenol-A feed all contribute to obtaining the desired tetrabromobisphenol-A product in an efficient manner. The selection of particular values for each of these process parameters to obtain the results desired will depend on each practitioner's needs and upon the equipment available. One practitioner may emphasize one benefit of using a process of this invention over other possible benefits. Thus, that practitioner may select different process parameter values than those selected by another practitioner who desires to highlight other benefit(s).

The use of the oxidation of the co-generated HBr to produce a part of the $Br_2$ needs for the processes of this invention is particularly attractive in those cases where the oxidation is more economical than the cost of providing for an equivalent amount of $Br_2$ in the feed to the reactor. The economic advantage is usually extant in those cases where the costs of feeding the entire amount of $Br_2$ used as $Br_2$ minus the value of recovered HBr is greater than the costs of feeding a lesser amount of $Br_2$ plus the oxidation of the HBr to provide the remainder of the bromine used in the bromination.

Though preferably designed to minimize the production of alkyl bromide, the processes of this invention are sufficiently adaptable to be modified to produce moderate amounts of methyl bromide or ethyl bromide, such as, for example, 20 lbs per 100 lbs of tetrabromobisphenol-A product. In this way, a future market need, even if greatly reduced, can be accommodated. When co-production of methyl bromide or ethyl bromide is utilized, the total $Br_2$ requirements of the process will be those amounts needed to produce the tetrabromobisphenol-A in a high yield and to produce the targeted amount of HBr. In these cases, the $Br_2$ feed and the amount of $Br_2$ generated from oxidation must be sufficient together to meet the bromine requirements of the process.

While the foregoing descriptions of the oxidation of HBr generally speak of the HBr being oxidized in the reactor or reaction mass, it is within the scope of the processes of this invention to also remove co-produced HBr from the reactor and oxidize it outside of the reactor and then to send the so produced $Br_2$ back to the reactor.

It is also within the scope of the processes of this invention to provide HBr to the reactor from a source other than the reaction in the reactor. This non-indigenous HBr can be oxidized along with the co-generated HBr to yield $Br_2$. The $Br_2$ produced from the non-indigenous HBr can then count against the total $Br_2$ needs of the process and the appropriate adjustment in the $Br_2$ feed can be made.

The process flow diagram of FIG. 1 constitutes an illustration of but one preferred way of carrying a process of this invention in which both recycle of underbrominated bisphenol-A, and in situ oxidation of hydrogen bromide co-product to form bromine in situ are utilized in the operation. It will be understood and appreciated that this particular flow diagram is not intended to constitute, and should not be construed as constituting, a limitation on the scope of this invention.

Referring to FIG. 1, in the plant layout schematically depicted the feeds to bromination reactor 10 are a bromine feed as at 12, an aqueous hydrogen peroxide feed as at 14, and a mixed feed stream of fresh bisphenol-A (BPA), recycled ethanol (EtOH) and recycled underbrominated bisphenol-A (represented for simplicity as TriBBPA) as at 16. The reaction mass from the bromination is transferred as at 18 to centrifuge 20. Centrifugation of the reaction mass separates the reaction mass into a liquids phase comprising ethanol, water and aqueous HBr which is transferred via line 22 to separator 30, and a wet cake of precipitate (crude product composed of tetrabromobisphenol-A and underbrominated bisphenol-A). The precipitate is transferred as at 24 to dissolver 40. Also fed to dissolver 40 at 42 is ethanol from storage in a quantity sufficient to dissolve the precipitate. Typically agitation is provided in dissolver 40 to assist in forming the solution therein. The resultant solution is then transferred as at 44 to recrystallizer 50 into which is also charged water as at 52 and the mixture is heated and then cooled to precipitate a purified tetrabromobisphenol-A (TBBPA) while leaving underbrominated in solution. The resultant slurry is transferred as at 54 to centrifuge 60 in which the purified tetrabromobisphenol-A solids phase is separated, recovered and transferred as at 62 to a dryer (not shown). The liquid phase from the centrifuigation in centrifuge 60 comprises ethanol, water and underbrominated bisphenol-A (represented for simplicity as TriBBPA), and is transferred as at 64 to separator 70 such as a still wherein the ethanol and water are distilled off, condensed and transferred as at 72 to separator 30. In the layout depicted the streams in 22 and 72 are merged before entering separator 30, but can of course be fed thereto as separate steams. In separator 30 ethanol is separated from the water and HBr. If desired and economically feasible, this aqueous HBr can be concentrated and used as feed at 14 to reactor 10, or it can be sent to facilities that either consume HBr as a reactant or in which the HBr is converted to bromine. The residue from separator 70, predominately underbrominated bisphenol-A, is transferred as at 74 to dissolver 80. Dissolver 80 also receives bisphenol-A as at 82. The ethanol from separator 30 is transferred as at 32 either to storage or as feed to dissolver 80 as needed to form therein the mixed feed stream of fresh bisphenol-A (BPA), recycled ethanol (EtOH) and recycled underbrominated bisphenol-A transmitted to reactor 10 as at 16. While the formation of such a mixed feed stream is desirable in order to ensure that the components thereof are in the desired proportions before entering the bromination reactor, it is possible to feed these components individually or as two separate solutions, one composed of bisphenol-A in ethanol and the other as underbrominated bisphenol-A in ethanol.

The following Examples are presented for purposes of illustration and not limitation. Example I illustrates a procedure for brominating bisphenol-A with a stoichiometric deficiency of bromine to produce both tetrabromobisphenol-A and underbrominated bisphenol-A. Examples II and III illustrate procedures that can be used to separate and recover the tetrabromobisphenol-A, while at the same time forming a solution of the underbrominated bisphenol-A which can be utilized for recycle to the bromination reaction.

EXAMPLE I

Underbromination of Bisphenol-A (BPA) in a Continuous Mode with in-situ Oxidation of HBr with $H_2O_2$ A three-liter flask was equipped with a mechanical stirrer, condenser, thermometer, and a down-drain to continually remove slurry from the reactor. The flask was fitted with a dip tube (⅛ inch O.D.) for feeding bromine vapor, and two feed tubes (⅛ inch O.D.) which terminated in the vapor phase, for feeding bisphenol-A solution and 50% $H_2O_2$ solution. The top of the condenser was connected to a vacuum pump. The temperature of the reactor was maintained at about 60° C. by controlling the vacuum at about 26 inches of Hg. BPA solution, $H_2O_2$ solution and bromine were fed to the reactor using peristaltic pumps. The bromine tube from the pump was connected to a nitrogen inlet and a bromine vaporizer (a flask heated with steam) and a gas outlet connected to the dip tube in the reactor. BPA solution was prepared by dissolving 4000 g of BPA in 4700 g of ethanol and 2000 g of water.

A 50 wt % solution (400 mL) of ethanol in water was charged to the reactor as the heel. BPA, $H_2O_2$ and bromine were fed to the reactor at flow rates of 26.5 mL/min., 2.35 mL/min and 5.1 mL/min. respectively. The BPA feed was kept stoichiometrically ahead of the available bromine in the reactor, and as a result the reaction mass remained colorless. The temperature of the reactor rose to about 60° C. and was kept at that temperature by reflux cooling. The product slurry was continually drained from the bottom of the reactor to keep a constant level in the reactor. The slurry was filtered and washed with 30 wt % aqueous ethanol. A second wash with deionized water was performed. The washed precipitate was dried and analyzed. HPLC analysis showed 86.55% of tetrabromobisphenol-A (TBBPA), 12.65% of tribromobisphenol-A, 0.16% of dibromobisphenol-A and less than 0.01% of tribromophenol. The mother liquor was found to contain 19.2 wt % HBr.

EXAMPLE II

Separation and Recovery of Tetrabromobisphenol-A and a Solution of Underbrominated Bisphenol-A A flask was charged with 10 g of the washed precipitated product from Example I, and 20 g of ethanol. The mixture was stirred and heated in an oil-bath at 70° C. to dissolve the solids. 10 g of deionized water was added dropwise to this solution over a period of 30 minutes. The heating was removed and the mixture was cooled to room temperature. The precipitate was filtered, washed with 50 wt % ethanol and dried to isolate 6.1 g (61% recovery) of TBBPA. HPLC analysis of this product showed 97.2% of TBBPA and 2.29% of tribromobisphenol-A.

EXAMPLE III

Separation and Recovery of Tetrabromobisphenol-A and a Solution of Underbrominated Bisphenol-A Another 10 g sample of the washed precipitated product from Example I was dissolved in 20 g of ethanol at 70° C. similar to the Example II procedure. 20 g of deionized water was added to the solution, and the solution was cooled to room temperature. The precipitate was filtered, washed with 50 wt % ethanol and dried to isolate 7.3 g (73% recovery) of TBBPA. HPLC analysis of this sample showed 95.73% of TBBPA and 3.84% of tribromobisphenol-A.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the preparation of tetrabromobisphenol-A, which process comprises:
    a) brominating bisphenol-A in a liquid phase reaction medium in which tetrabromobisphenol-A is relatively insoluble, using a stoichiometric deficiency of bromine to thereby form in the reaction mass a precipitate consisting essentially of about 50 to about 95 wt % of tetrabromobisphenol-A and about 50 to about 5 wt % of underbrominated bisphenol-A;
    b) recovering precipitate from the reaction mass; and
    c) recovering tetrabromobisphenol-A from the precipitate.

2. A process of claim 1 wherein said medium in a) includes water.

3. A process of claim 1 wherein said medium in a) includes water and a water-miscible alcohol.

4. A process of claim 1 wherein said medium in a) includes water and ethanol.

5. A process for the preparation of tetrabromobisphenol-A, which process comprises:
   a) brominating bisphenol-A and underbrominated bisphenol-A in a liquid phase reaction medium in which tetrabromobisphenol-A is relatively insoluble, using a stoichiometric deficiency of bromine to thereby form in the reaction mass a precipitate consisting essentially of about 50 to about 95 wt % of tetrabromobisphenol-A and about 50 to about 5 wt % of underbrominated bisphenol-A;
   b) recovering precipitate formed in the bromination;
   c) separating tetrabromobisphenol-A and underbrominated bisphenol-A from each other, recovering tetrabromobisphenol-A, and recycling underbrominated bisphenol-A to a).

6. A process of claim 5 wherein the separation in b) is carried out at least periodically during the bromination being conducted in a).

7. A process of claim 5 wherein the separation in b) is carried out substantially continuously as precipitate is being formed during the bromination being conducted in a).

8. A process of claim 5 wherein said medium in a) includes water.

9. A process of claim 5 wherein tetrabromobisphenol-A and underbrominated bisphenol-A are separated from each other in c) by recrystallizing tetrabromobisphenol-A from a solution of tetrabromobisphenol-A and underbrominated bisphenol-A, and separating the recrystallized tetrabromobisphenol-A from the residual solution of underbrominated bisphenol-A.

10. A process of claim 9 wherein underbrominated bisphenol-A is recovered from said residual solution before recycle to a).

11. A process of claim 5 wherein said medium in a) includes water; wherein the separation in b) is carried out at least periodically during the bromination being conducted in a); and wherein tetrabromobisphenol-A and underbrominated bisphenol-A are separated from each other in c) by recrystallizing tetrabromobisphenol-A from a solution of tetrabromobisphenol-A and underbrominated bisphenol-A, and separating the recrystallized tetrabromobisphenol-A from the residual solution of underbrominated bisphenol-A.

12. A process of claim 5 wherein said medium in a) includes water; wherein the separation in b) is carried out substantially continuously as precipitate is being formed during the bromination being conducted in a); and wherein tetrabromobisphenol-A and underbrominated bisphenol-A are separated from each other in c) by recrystallizing tetrabromobisphenol-A from a solution of tetrabromobisphenol-A and underbrominated bisphenol-A, and separating the recrystallized tetrabromobisphenol-A from the residual solution of underbrominated bisphenol-A.

13. A process of any of claims 5–12 wherein at least periodically during the bromination in a), at least elemental bromine, an aqueous hydrobromic acid solution, and aqueous hydrogen peroxide are fed into the liquid phase reaction medium.

14. A process of claim 13 wherein the elemental bromine is fed into said medium as gaseous bromine, and wherein the feed entry point for the gaseous bromine into said medium is within the body of said medium below the upper surface thereof.

15. A process of any of claims 5–12 wherein the liquid phase reaction medium in a) is comprised predominately of water and a water-miscible alcohol, and wherein at least periodically during the bromination in a), at least bisphenol-A, underbrominated bisphenol-A, elemental bromine, a water-miscible alcohol, an aqueous hydrobromic acid solution, and aqueous hydrogen peroxide are fed into the liquid phase reaction medium.

16. A process of claim 15 wherein the water-miscible alcohol is ethanol, and wherein the water:ethanol weight ratio in the reaction mass is maintained substantially within the range of about 15:85 to about 70:30 during the bromination in a).

17. A process of any of claims 5–12 wherein the bromination is performed in a batch mode.

18. A process of any of claims 5–12 wherein the bromination is performed in a continuous mode.

19. A process for the preparation of tetrabromobisphenol-A, which process comprises:
   a) feeding to a reactor at least bisphenol-A, underbrominated bisphenol-A, a water-miscible solvent, bromine, water, and an oxidant to at least partially form a reaction mass having a liquid phase in which tetrabromobisphenol-A is relatively insoluble;
   b) substantially throughout the feed in a), providing for the presence of a stoichiometric deficiency of bromine relative to the bisphenol-A and underbrominated bisphenol-A to thereby form in the reaction mass, a precipitate consisting essentially of about 50 to about 95 wt % of tetrabromobisphenol-A and about 50 to about 5 wt % of underbrominated bisphenol-A;
   c) removing precipitate and optionally a portion of the reaction mass from the reactor; and
   d) separating tetrabromobisphenol-A and underbrominated bisphenol-A from each other.

20. A process of claim 19 wherein underbrominated bisphenol-A from d) is recycled as feed to a).

21. A process of claim 19 wherein the precipitate formed in b) consists essentially of about 80 to about 95 wt % of tetrabromobisphenol-A, about 20 to about 5 wt % of underbrominated bisphenol-A, and, if any, no more than about 0.1 wt % of tribromophenol.

22. A process of claim 21 wherein underbrominated bisphenol-A from d) is recycled as feed to a).

23. A process of claim 19 wherein tetrabromobisphenol-A and underbrominated bisphenol-A are separated from each other in d) by recrystallizing tetrabromobisphenol-A from a solution of tetrabromobisphenol-A and underbrominated bisphenol-A, and separating the recrystallized tetrabromobisphenol-A from the residual solution of underbrominated bisphenol-A.

24. A process of claim 23 wherein said solution of tetrabromobisphenol-A and underbrominated bisphenol-A is a solution in a water-miscible alcohol to which water is added during the recrystallization.

25. A process of claim 19 wherein the water-miscible solvent in a) is a water-miscible alcohol; wherein tetrabromobisphenol-A and underbrominated bisphenol-A are separated from each other in d) by recrystallizing tetrabromobisphenol-A from a solution of tetrabromobisphenol-A and underbrominated bisphenol-A in a water-miscible alcohol to which water is added during the recrystallization, and separating the recrystallized tetrabromobisphenol-A from the residual aqueous alcoholic solution of underbrominated bisphenol-A.

26. A process of claim 25 wherein the water-miscible alcohol in a) and the water-miscible alcohol used in forming the solution from which tetrabromobisphenol-A is recrystallized have the formula ROH where the R is an alkyl group and where the alkyl group in both said water-miscible alcohols is the same; and wherein at least a portion of the underbrominated bisphenol-A and at least a portion of the water-miscible alcohol solvent are recovered from said residual aqueous alcoholic solution for recycle to a).

27. A process of any of claims 19–26 wherein in c) precipitate and a portion of the reaction mass are removed at least periodically from the reactor during the bromination of bisphenol-A and underbrominated bisphenol-A, and wherein the total volume of the feeds to the reactor and the volume of the precipitate and portion of the reaction mass removed from the reactor are controlled to keep the volume of the reaction mass in the reactor substantially constant throughout substantially the entire bromination reaction.

28. A process of claim 19 or 20 wherein the elemental bromine is fed into the reaction mass as gaseous bromine, and wherein the feed entry point for the gaseous bromine is within the body of the liquids in the reaction mass below the upper surface thereof.

29. A process of claim 19 or 20 wherein the water-miscible solvent is an alcohol and wherein the oxidant is hydrogen peroxide.

30. A process of claim 29 wherein the alcohol is ethanol, and wherein the water:ethanol weight ratio in the reaction mass is maintained substantially within the range of about 15:85 to about 70:30 during the bromination.

31. A process of claim 19 or 20 wherein the bromination in said reactor is performed in a batch mode.

32. A process of claim 19 or 20 wherein the bromination in said reactor is performed in a continuous mode.

33. A process of claim 19 wherein in a) the elemental bromine is fed into the reaction mass as gaseous bromine; wherein the feed entry point for the gaseous bromine is within the body of the liquids in the reaction mass below the upper surface thereof; wherein in c) precipitate and a portion of the reaction mass are removed at least periodically from the reactor during the bromination of bisphenol-A and underbrominated bisphenol-A; and wherein the total volume of the feeds to the reactor and the volume of the precipitate and portion of the reaction mass removed from the reactor are controlled to keep the volume of the reaction mass in the reactor substantially constant throughout substantially the entire bromination reaction.

34. A process of claim 33 wherein underbrominated bisphenol-A from d) is recycled as feed to a).

35. A process for the preparation of tetrabromobisphenol-A, which process comprises:
  a) feeding, to a reactor, a solution comprised of bisphenol-A, water and a water-miscible solvent to at least partially form a reaction mass having a liquid phase containing an amount of water in the range of from above about 15 to about 65 wt % water that renders tetrabromobisphenol-A substantially insoluble in said liquid phase, the wt % being based upon the amount of water and water-miscible solvent in the liquid phase;
  b) during a), providing for the presence of $Br_2$ in the reaction mass to produce tetrabromobisphenol-A and HBr co-product;
  c) oxidizing HBr produced in the reaction mass to yield $Br_2$;
  d) having a reaction mass temperature which is within the range of from about 50 to about 100° C.;
  e) keeping the total amount of bromine provided in a) and produced in c) sufficiently below the stoichiometric amount required to convert all of the bisphenol-A present in the reactor to tetrabromobisphenol-A so that a precipitate is formed composed of about 50 to about 95 wt % of tetrabromobisphenol-A and about 50 to about 5 wt % of underbrominated bisphenol-A.

36. A process of claim 35 wherein tetrabromobisphenol-A from e) is recovered, wherein underbrominated bisphenol-A from e) is recycled as feed to a), and wherein the total amount of bromine provided in a) and produced in c) is kept sufficiently below the stoichiometric amount to form the precipitate specified in e).

37. A process of claim 35 or 36 wherein the water-miscible solvent is methanol or ethanol.

38. A process for the preparation of tetrabromobisphenol-A, which process comprises:
  a) feeding to a reactor at least bisphenol-A, underbrominated bisphenol-A, a water-miscible solvent, bromine, and water to at least partially form a reaction mass having a liquid phase in which tetrabromobisphenol-A is relatively insoluble;
  b) substantially throughout the feed in a), providing for the presence of a stoichiometric deficiency of bromine relative to the bisphenol-A and underbrominated bisphenol-A to thereby form in the reaction mass, a precipitate consisting essentially of about 50 to about 95 wt % of tetrabromobisphenol-A and about 50 to about 5 wt % of underbrominated bisphenol-A;
  c) removing from the reactor at least a portion of the reaction mass including precipitate;
  d) separating tetrabromobisphenol-A and underbrominated bisphenol-A from each other; and
  e) recycling underbrominated bisphenol-A as feed in a).

39. A process of claim 38 wherein portions of the reaction mass including precipitate are removed from the reactor continuously or intermittently during the bromination, and wherein the total volume of the feeds to the reactor and the volume of the portions of the reaction mass including precipitate removed from the reactor are controlled to keep the volume of the reaction mass in the reactor substantially constant throughout substantially the entire bromination reaction.

40. A process of claim 38 or 39 wherein said precipitate consists essentially of about 80 to about 95 wt % of tetrabromobisphenol-A, about 20 to about 5 wt % of underbrominated bisphenol-A, and, if any, no more than about 0.1 wt % of tribromophenol.

41. A process of claim 1 wherein the precipitate formed in a) consists essentially of about 80 to about 95 wt % of tetrabromobisphenol-A, about 20 to about 5 wt % of underbrominated bisphenol-A, and, if any, no more than about 0.1 wt % of tribromophenol.

42. A process of claim 5 wherein the precipitate formed in a) consists essentially of about 80 to about 95 wt % of tetrabromobisphenol-A, about 20 to about 5 wt % of underbrominated bisphenol-A, and, if any, no more than about 0.1 wt % of tribromophenol.

43. A process of claim 35 or 36 wherein the precipitate formed in e) consists essentially of about 80 to about 95 wt % of tetrabromobisphenol-A, about 20 to about 5 wt % of underbrominated bisphenol-A, and, if any, no more than about 0.1 wt % of tribromophenol.

* * * * *